United States Patent
Samuel et al.

(10) Patent No.: US 10,434,515 B2
(45) Date of Patent: Oct. 8, 2019

(54) THERMAL GRADIENT PLUG FLOW MICROFLUIDIC DEVICES FOR EXTREME PCR

(71) Applicant: University of Utah Research Foundation, Salt Lake City, UT (US)

(72) Inventors: Raheel Samuel, Salt Lake City, UT (US); Bruce Gale, Salt Lake City, UT (US); Alex Jafek, Salt Lake City, UT (US); James Trauba, Salt Lake City, UT (US); Kenneth Aston, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 171 days.

(21) Appl. No.: 15/724,066

(22) Filed: Oct. 3, 2017

(65) Prior Publication Data

US 2018/0093273 A1     Apr. 5, 2018

Related U.S. Application Data

(60) Provisional application No. 62/403,521, filed on Oct. 3, 2016.

(51) Int. Cl.
*B01L 7/00*        (2006.01)
*C12Q 1/68*      (2018.01)
(Continued)

(52) U.S. Cl.
CPC .......... *B01L 7/525* (2013.01); *B01L 3/502715* (2013.01); *B01L 3/502784* (2013.01);
(Continued)

(58) Field of Classification Search
CPC .............. C12Q 1/686; C12Q 2565/629; B01L 2200/0673; B01L 2200/143;
(Continued)

(56) References Cited

U.S. PATENT DOCUMENTS 8,263,392 B2 *   9/2012   Gale ................. B01L 3/502707
                                                          435/288.5
8,975,027 B2     3/2015   Gale et al.
(Continued)

FOREIGN PATENT DOCUMENTS

WO    WO 2013/177429 A2    11/2013
WO    WO 2015/069743 A1    5/2015

*Primary Examiner* — Jennifer Wecker
(74) *Attorney, Agent, or Firm* — Thorpe North & Western, LLP

(57) ABSTRACT

A microfluidic device can include a temperature regulator positioned to generate a temperature gradient across a thermally controlled portion of the microfluidic device from a high temperature region to a low temperature region. Additionally, the microfluidic device can include a bi-directional microfluidic serpentine pathway having a first terminus and a second terminus. The bi-directional microfluidic serpentine pathway can be oriented along a longitudinal direction transverse to the temperature gradient. Further, the bi-directional microfluidic serpentine pathway can include a plurality of oscillation segments fluidly coupling the first terminus to the second terminus and forming a flow path adapted to oscillate a fluid between the high temperature region and the low temperature region. The bi-directional microfluidic serpentine pathway can have a uniform cross section to facilitate bi-directional flow.

33 Claims, 3 Drawing Sheets

(51) Int. Cl.
   *B01L 3/00* (2006.01)
   *C12Q 1/686* (2018.01)
(52) U.S. Cl.
   CPC . *B01L 2200/0673* (2013.01); *B01L 2200/143* (2013.01); *B01L 2200/147* (2013.01); *B01L 2300/0883* (2013.01); *B01L 2300/18* (2013.01); *C12Q 1/686* (2013.01)
(58) Field of Classification Search
   CPC ....... B01L 2200/147; B01L 2300/0883; B01L 2300/18; B01L 3/502715; B01L 3/502784; B01L 7/525
   See application file for complete search history.

(56) References Cited

U.S. PATENT DOCUMENTS

| | | | |
|---|---|---|---|
| 2015/0031087 A1* | 1/2015 | Nagai | C12Q 1/686 435/91.2 |
| 2015/0118715 A1 | 4/2015 | Wittwer et al. | |
| 2016/0289736 A1 | 10/2016 | Jones et al. | |

* cited by examiner

THERMAL GRADIENT PLUG FLOW MICROFLUIDIC DEVICES FOR EXTREME PCR

RELATED APPLICATION(S)

This application claims the benefit of U.S. Provisional Patent Application No. 62/403,521, filed on Oct. 3, 2016, which is incorporated herein by reference.

GOVERNMENT INTEREST

None.

BACKGROUND

Polymerase chain reaction (PCR) is one of the most important reactions in molecular diagnostics. It derives its name from one of its key components, a DNA polymerase used to amplify a piece of DNA by in vitro enzymatic replication. As PCR progresses, the DNA generated (the amplicon) is itself used as a template for replication. This sets in motion a chain reaction in which the DNA template is exponentially amplified. With PCR, it is possible to amplify a single or few copies of a piece of DNA across several orders of magnitude, generating millions or more copies of the DNA piece. PCR employs a thermostable polymerase, dNTPs, and a pair of primers.

PCR is conceptually divided into three reactions, each usually assumed to occur over time at each of three temperatures. Such an "equilibrium paradigm" of PCR is easy to understand in terms of three reactions (denaturation, annealing, and extension) occurring at three temperatures over three time periods each cycle. However, this equilibrium paradigm does not fit well with physical reality. Instantaneous temperature changes do not occur; it takes time to change the sample temperature. Furthermore, individual reaction rates vary with temperature, and once primer annealing occurs, polymerase extension immediately follows. More accurate, particularly for rapid PCR, is a kinetic paradigm where reaction rates and temperature are always changing. Holding the temperature constant during PCR is not necessary as long as the products denature and the primers anneal. Under the kinetic paradigm of PCR, product denaturation, primer annealing, and polymerase extension may temporally overlap and their rates continuously vary with temperature. Under the equilibrium paradigm, a cycle is defined by three temperatures each held for a time period, whereas the kinetic paradigm requires transition rates and target temperatures.

SUMMARY

A microfluidic device can include a temperature regulator positioned to generate a temperature gradient across a thermally controlled portion of the microfluidic device from a high temperature region to a low temperature region. Additionally, the microfluidic device can include a bi-directional microfluidic serpentine pathway having a first terminus and a second terminus. The bi-directional microfluidic serpentine pathway can be oriented along a longitudinal direction transverse to the temperature gradient. Further, the bi-directional microfluidic serpentine pathway can include a plurality of oscillation segments fluidly coupling the first terminus to the second terminus and forming a flow path adapted to oscillate a fluid between the high temperature region and the low temperature region as the pathway migrates along the longitudinal direction. The bi-directional microfluidic serpentine pathway can have a uniform cross section to facilitate bi-directional flow.

A method of amplifying a nucleic acid can include introducing a nucleic acid sample into a microfluidic serpentine pathway having a plurality of oscillation segments and a uniform cross-section to facilitate bi-directional fluid flow. The nucleic acid sample can include the nucleic acid. The method can also include directing the nucleic acid sample along the microfluidic serpentine pathway through a plurality of alternating high temperature zones and low temperature zones via the plurality of oscillation segments. The plurality of alternating high temperature zones and low temperature zones can provide a temperature gradient suitable to amplify the nucleic acid.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1A:
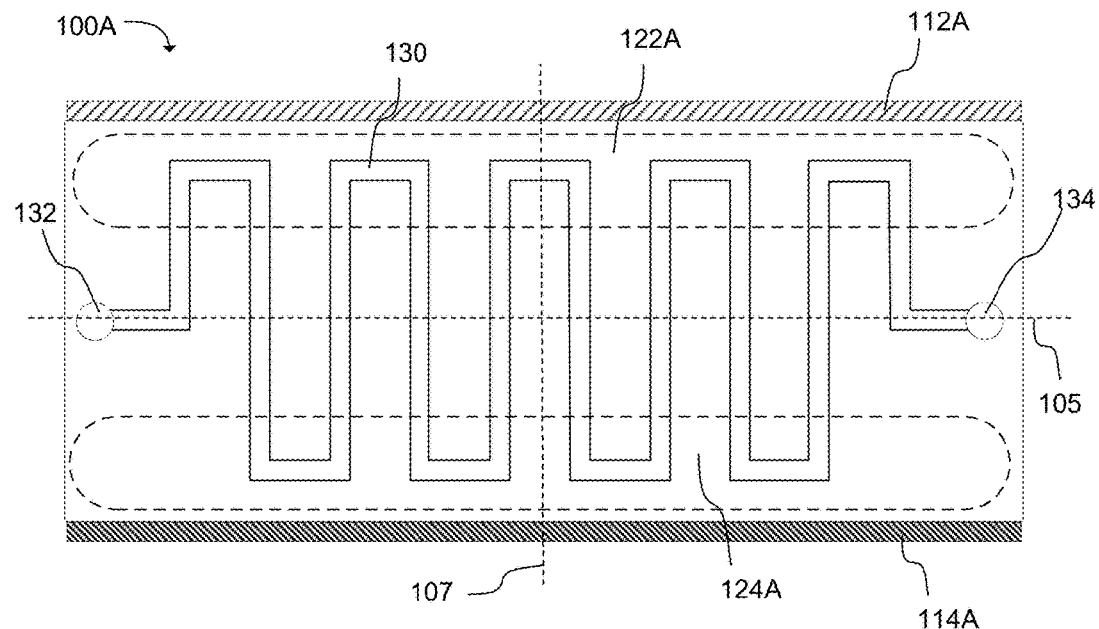
FIG. 1A illustrates a top view of a microfluidic device, in accordance with examples of the present disclosure.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a nucleic acid" includes reference to one or more of such materials and reference to "directing" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 5%, and most often less than 1%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of" For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Microfluidic Devices

The present disclosure describes microfluidic devices that can be used to perform extreme polymerase chain reaction (PCR). Generally, the microfluidic device can include a temperature regulator positioned to generate a temperature gradient across a thermally controlled portion of the microfluidic device from a high temperature region to a low temperature region. Additionally, a microfluidic device also generally includes a bi-directional microfluidic serpentine pathway having a first terminus and a second terminus. The microfluidic pathway can be oriented along a longitudinal direction transverse to the temperature gradient. The microfluidic pathway can include a plurality of oscillation segments fluidly coupling the first terminus to the second terminus and forming a flow path adapted to oscillate a fluid between the high temperature region and the low temperature region. Further, the microfluidic pathway generally has a uniform cross-section to facilitate bi-directional fluid flow, though this not always required.

One example of a microfluidic device 100A is illustrated in FIG. 1A. In this particular example, the microfluidic device 100A has a plurality of temperature regulators 112A, 114A. Specifically, temperature regulator 112A can be a heat source and temperature regulator 114A can be a cooling source. Thus, during use, the heat source 112A can provide the microfluidic device with a high temperature region 122A. As such, even if cooling source 114A is not employed in microfluidic device 110A, a temperature gradient can be established along a latitudinal direction of the device from the high temperature region 122A to a low temperature region 124A remote from and opposite to the high temperature region 122A. For reference in the present discussion, longitudinal axis 105 and latitudinal axis 107 have been included in FIG. 1A. Further, while not expressly depicted in the other device figures, these axes still generally apply to the other device figures. It is further noted that the areas 122A and 124A are marked for ease of discussion with respect to the microfluidic device 100A. These markings are not intended to form any actual boundaries of the high temperature region or low temperature region present on the device during use. As described above, in order to establish a suitable temperature gradient across the microfluidic device, the use of a heat source 112A alone can be sufficient. However, in some examples, it can be advantageous to further employ a cooling source 114A. In some examples, employing both a heat source 112A and a cooling source 114A can provide the end user with greater control over the temperature gradient, and any desired changes thereto, than employing only a heat source 112A. This can be a desirable feature when the end user wants to make real-time adjustments to the temperature gradient, such as to increase a rate of amplification of a particular nucleic acid. Furthermore, these temperature regions do not necessarily dictate that constant temperature or a gradient exists within these regions or in between the two regions. For example, in most cases a temperature gradient may exist across the entire latitudinal direction of the device. In such cases, the high temperature region will be maintain within a desired target range as dictated by particular PCR chemistry. Similarly, the low temperature region can be maintained in a relatively lower temperature range. Intermediate regions will exhibit corresponding gradual temperature gradient (e.g. decrease) from the high to low temperature region.

Figure 1B:
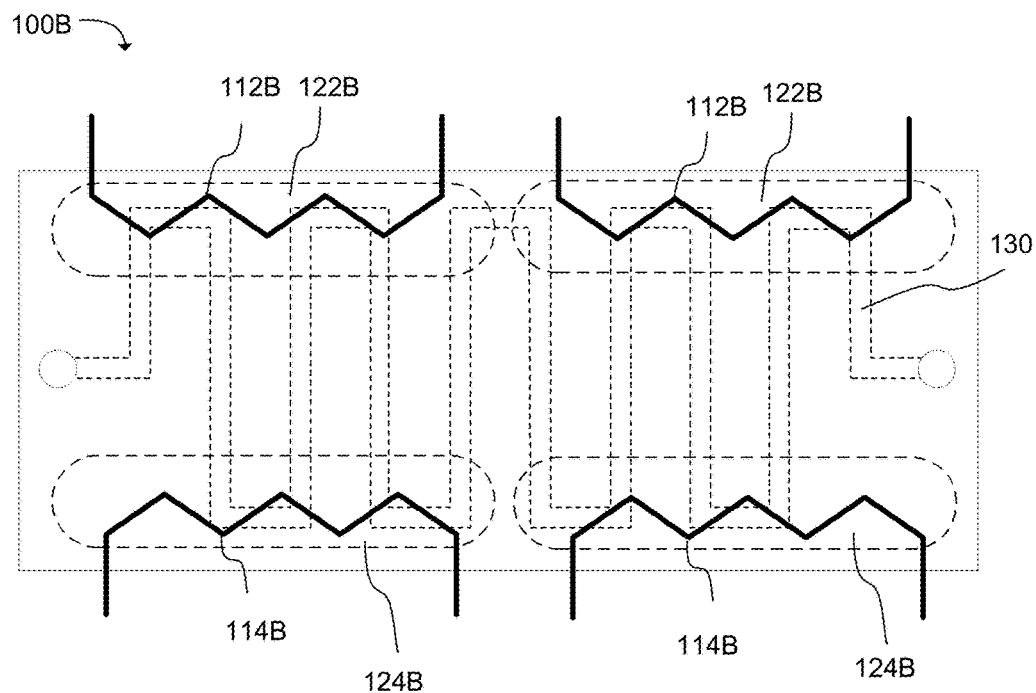
FIG. 1B illustrates a bottom view of a microfluidic device, in accordance with examples of the present disclosure.

It is further noted that the temperature regulators 112A and 114A illustrated in FIG. 1A can be disposed within a common plane of the device. Alternatively, one or both of the temperature regulators 112A and 114A can be oriented adjacent a plane of the microfluidic pathways to provide an offset heat transfer path. As an alternative or additional option, FIG. 1B illustrates a bottom view of microfluidic device 100B that includes a plurality of heat sources 112B and a plurality of cooling sources 114B oriented in a common plane of the device. In this particular example, the heat sources 112B and cooling sources 114B are positioned toward a bottom of the device 100B, but the heat sources 112B and/or cooling sources could additionally or alternatively be positioned toward a top of the device. Although heating and/or cooling sources are often operated uniformly (e.g. so as to form a longitudinally uniform temperature), in some cases the heating and/or cooling sources can be operated independently to create high temperature sub-regions and/or low temperature sub-regions.

Accordingly, each of the heat sources 112B and cooling sources 114B illustrated in FIG. 1B can be individually controllable. Thus, each of the heat sources 112B and cooling sources 114B can be adjusted or turned on/off as desired. As such, each of the heat sources 112B can be used to provide distinct high temperature regions 122B. Similarly, each of the cooling sources 114B can be used to provide distinct low temperature regions 124B. However, in some examples, each of the heat sources 112B can be operated at the same temperature to establish a high temperature region equivalent to that illustrated in FIG. 1A. Likewise, in some examples, each of the cooling sources 114B can be operated at the same temperature to establish a low temperature region equivalent to that illustrated in FIG. 1A. While FIG. 1B illustrates only two heat sources 112B and two cooling sources 114B, any suitable number of heat sources and cooling sources can be used, each of which can be individually controllable. In some examples, a distinct heat source, and optionally cooling source, can be employed for each region of the device intended to provide one PCR thermal cycle. In yet other examples, a single heat source, and optionally cooling source, can be employed for a region of the device intended to provide multiple PCR thermal cycles. Thus, the device can typically maintain longitudinally isothermal conditions with a desired temperature gradient transverse to the longitudinal axis of the device.

Figure 2:
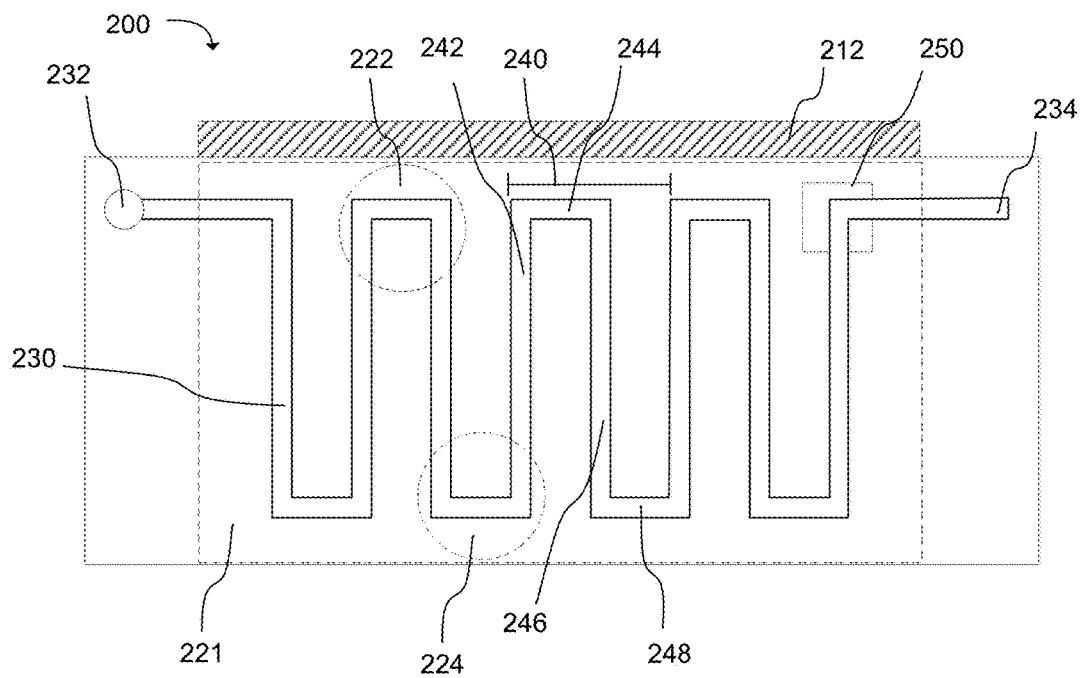
FIG. 2 illustrates a top view of another microfluidic device, in accordance with examples of the present disclosure.

It is noted that when one or more heat sources 112B and corresponding cooling sources 114B are turned off, the thermally controlled portion of the microfluidic device 100B can be adjusted. For example, where the heating source 112B and the cooling source 114B on a common longitudinal end of the device 100B are both turned off, approximately one half of the device 100B can remain thermally controlled, whereas the other approximately one half of the device is not. Thus, the temperature regulator of the device is thermally associated with the thermally controlled portion of the device. It is noted that, in some examples, the thermally controlled portion of the device can include the whole device. Alternatively, as illustrated in FIG. 2, a thermally controlled portion 221 can be smaller than the entire device 200. In this specific example, the heat source 212 does not extend the entire length of the device 200. As such, the longitudinal ends of the device 200 are not thermally controlled (i.e. do not form part of the temperature gradient from the high temperature region proximate the heat source 212 to the low temperature region distal to the heat source 212). The thermally controlled portion of the device can be adjusted to control the number of PCR thermal cycles achieved for a given use of the device, as will be described in further detail below.

A variety of temperature regulators can be employed in the microfluidic devices described herein. Non-limiting examples can include an electrical resistor, a Peltier heat pump, a heat transfer fluid, thermoelectric materials, chemical reactions (e.g. phase change, combustion, etc.), irradiation (e.g. infrared, microwave, solar, ultraviolet, ultrasound, etc.), a heat sink, forced convection, the like, or a combination thereof. In some specific examples, the heat source can be a thin-film heater. In some additional examples, heating and/or cooling the device can employ a thermally conductive material as an intermediate heat transfer material, which can optionally be in direct contact with the thermal regulator. In some examples, the thermally conductive material can be positioned in plane with the device or form the microfluidic pathways (e.g. used as a starting substrate from which microfluidic pathways are formed). In some additional examples, the thermally conductive material can be positioned out of plane with the device to provide an offset heat transfer path. For example, a heat transfer plate can be oriented along a backside of the microfluidic substrate. Non-limiting examples of thermally conductive materials can include a metal plate, such as aluminum, copper, silver, etc., graphite, hexagonal boron nitride, thermally conductive polymers, etc. In some specific examples, microfluidic device can employ a Peltier heat pump. Where this is the case, the microfluidic device can further employ n-type and p-type semiconductor materials in connection with a thermally conductive material disposed on opposing sides of the device, for example. The thermally conductive materials can be positioned where the high temperature and low temperature regions are desired to be formed. The n-type and p-type semiconductor materials can be positioned such that when a voltage is applied to the two semiconductor materials, the current across the junction of the semiconductors causes a temperature difference to form the high temperature region and the low temperature region at the oppositely disposed thermally conductive materials. It is additionally noted that various combinations of temperature regulators can also be used, as desired.

In some examples, it can be desirable to achieve a steady state temperature prior to performing PCR with the microfluidic device. As such, in some examples, it can be advantageous to include one or more temperature sensors on the device, such as temperature sensor 250 illustrated in FIG. 2. It is noted that while only one temperature sensor 250 is illustrated on device 200, more than one temperature sensor 250 can be valuable in measuring steady state temperature, measuring temperature of a specific location, etc. Thus, one or a plurality of temperature sensors can be included in the high temperature region, the low temperature region, or elsewhere on the device. In one example, a single high temperature sensor can be oriented within the high temperature region and a single low temperature sensor can be oriented within the low temperature region. A variety of temperature sensors can be employed in the device, such as but not limited to, a thermocouple, a thermistor, a resistance temperature detector (RTD), the like, or a combination thereof. Additional temperature sensors can aid in confirming and regulating temperature with precision, but can also increase cost and complexity.

Turning again to FIG. 1A, the microfluidic device 100A also includes a bi-directional microfluidic serpentine pathway 130. The microfluidic pathway 130 can include a first terminus 132 and a second terminus 134. It is noted that in some examples, the first terminus 132 and the second terminus 134 can both be inlet/outlet termini, such that either of the termini can be used to introduce a fluid into the microfluidic pathway 130 and/or act as a connection point for a microfluidic pump. However, in some examples, one of the first terminus 132 and the second terminus 134 is not an inlet/outlet terminus (i.e. the terminus can be a dead end). In some examples, either the first terminus 132 or the second terminus 134 can include an expandable membrane where fluid and pressure can build up and be pushed back toward the other terminus. One example of a microfluidic pathway having only one inlet/outlet terminus is illustrated in FIG. 2. Specifically, microfluidic device 200 includes a microfluidic pathway 230 that includes a first terminus 232 that is an inlet/outlet terminus and a second terminus 234 that is not an inlet/outlet terminus (i.e. is a dead end terminus).

Turning again to FIG. 1A, the bi-directional microfluidic serpentine pathway 130 can be oriented along a longitudinal direction transverse to the temperature gradient. Thus, as a fluid is directed along the microfluidic pathway from one terminus (e.g. terminus 132) to the other terminus (e.g. terminus 134), the fluid travels in a serpentine manner transverse to the temperature gradient formed from the high temperature region to the low temperature region. As used herein, transverse means non-parallel, in some cases, perpendicular, and in most case within about 10° of perpendicular.

In some examples, the bi-directional microfluidic serpentine pathway can be longitudinally symmetrical, as illustrated in each of FIGS. 1A, 1B, and 2. However, in some examples, the bi-directional microfluidic serpentine pathway can be longitudinally asymmetrical, for example when reuse of channels is not required for thermocycling. Further, in some examples, the bi-directional microfluidic serpentine pathway can be positioned within a common plane. In yet other examples, the bi-directional microfluidic serpentine pathway can traverse adjacent planes such that it is not positioned solely within a common plane. For example, spiral or stacked microfluidic channels can be formed. In one example, multiple serpentine pathways such as those illustrated in FIG. 1A can be stacked adjacent one another to form multiple parallel pathway planes having an interconnecting conduit to allow the fluid plug and motive fluids to pass from one plane to an adjacent plane. This can allow for a reduction in length of the device, for example.

Turning now to FIG. 2, the bi-directional microfluidic serpentine pathway 230 can include a plurality of oscillation segments 240. It is noted that the marking of the particular segment 240 is somewhat arbitrary, as the oscillation segment can be defined as any segment of the microfluidic pathway 230 having a regular periodicity. Generally, an oscillation segment corresponds to a portion of the pathway 230 that provides one PCR thermal cycle or amplification cycle per unidirectional pass of a sample fluid. However, for the present discussion, segment 240, and corresponding periodic segments, are defined as oscillation segments. In some examples, the oscillation segment 240 can include a first lateral segment 242 directing fluid to the high temperature region proximate the heat source 212, a second lateral segment 246 directing fluid to the low temperature region distal to the heat source 212, and a first longitudinal segment 244 fluidly interconnecting the first lateral segment 242 and the second lateral segment 246 within the high temperature region. It is noted that these particular segments of the oscillation segment 240 are defined with respect to the fluid flowing from the first terminus 232 to the second terminus 234. However, where the fluid flow is reversed, the first and second lateral segments would likewise be reversed such that the first lateral segment would be segment 246 and the second lateral segment would be segment 242. Further in some examples, the oscillation segment 240 can further include a second longitudinal segment 248. The second longitudinal segment 248 can fluidly connect adjacent lateral segments within the low temperature region. As a general rule the lateral segments can have a larger length than longitudinal segments. In some cases, the ratio of lateral to longitudinal lengths can be from 2:1 to 100:1, and in some cases about 4:1 to 50:1.

As illustrated in FIG. 2, each of the oscillation segments 240 is generally positioned within the thermally controlled region 221. However, this can depend on the number of PCR thermal cycles that are desired to be achieved for each pass of a sample through the pathway 230. For example, turning again to FIG. 1B, where the heat source 112B and corresponding cooling source 114B of one longitudinal end of device 100B are turned off, the effective thermally controlled region is reduced to approximately one half of the device. As such, the number of PCR thermal cycles achievable from one bi-directional pass of a nucleic acid sample with device 100B can be adjusted from about 10 to about 6 simply by turning off half of the temperature regulators and reducing the overall thermally controlled region. This can allow the user to customize the number of PCR thermal cycles per unidirectional or bi-directional pass of the sample.

Turning again to FIG. 2, as described above, each of the oscillation segments 240 generally corresponds to the portion of pathway 230 that provides one PCR thermal cycle per unidirectional pass. Specifically, as fluid is directed toward the high temperature region proximate the heat source 212, the fluid will enter a heated zone 222. Subsequently, the fluid will be directed toward the low temperature region distal to the heat source 212 and enter a low temperature zone 224. This temperature cycle occurs within one oscillation segment, such as oscillation segment 240. Thus, the plurality of oscillation segments 240 form a flow path adapted to oscillate a fluid between high temperature zones and low temperature zones, or the high temperature region and the low temperature region. In other words, the plurality of oscillation segments 240 can form peaks and troughs along the serpentine pathway that intersect with the high temperature region and the low temperature region, respectively.

The number of oscillation segments on a particular device can be adjusted as desired by the end user to achieve a particular number of PCR thermal cycles per unidirectional or bi-directional pass of a sample. For example, in some cases, the microfluidic device can include from about 5 oscillation segments to about 50 oscillation segments. In other examples, the microfluidic device can include from about 10 oscillation segments to about 35 oscillation segments, or from about 20 oscillation segments to about 40 oscillation segments. Thus, where the microfluidic device includes 30 oscillation segments, for example, a single unidirectional pass can provide 30 PCR thermal/amplification cycles, whereas a single bi-directional pass (i.e. device cycle) can provide 60 PCR thermal/amplification cycles.

The oscillation segments can have a variety of configurations. In some examples, as illustrated in FIGS. 1A, 1B, and 2, each of the oscillation segments can include a right-angle bend with a squared corner, or can be entirely formed of segments interconnected at right-angle bends with squared corners. However, this is not required. In some examples, the oscillation segments can have a Z-shape, an S-shape, the like, or a combination thereof. Thus, oscillation segments within a common device need not be the same shape. In some examples, the oscillation segments can still have sharp corners, rather than rounded corners, even when the individual segments are not interconnected at right-angles.

It is further noted that the microfluidic pathway can generally have a uniform cross section along the entire length of the pathway. This, among other things, can facilitate bi-directional flow between the first and second terminus. However, this is not expressly required. Employing a microfluidic pathway with a uniform cross section can also help minimize bubble formation during use, whereas a non-uniform cross section can result bubble formation within the microfluidic pathway. Uniform cross section area also maintains a constant flow velocity of the plug along the pathway (assuming a constant driving force). Further, a non-uniform cross section can change the period of time a sample is exposed to high and low temperatures during a single pass. While this can be advantageous for a single unidirectional pass through the microfluidic pathway, in some cases, this can reduce or minimize the effectiveness of bi-directional flow through the microfluidic pathway. This is because a non-uniform cross section is typically optimized for fluid flow in a given single direction. Thus, when the fluid flow is reversed, the previously optimized conditions become disadvantageous conditions in the reverse direction. However, in some cases, a microfluidic pathway can be prepared with a non-uniform cross section, but that does not expose the sample to different conditions depending on the direction of fluid flow. Typically for a rectangular channel, the cross section height can be from about 10 µm to about 500 µm, and in most cases from about 75 µm to about 250 µm, and in one example 100 µm. Similarly, rectangular channel width can range from about 100 µm to about 600 µm, and in most cases from about 300 µm to about 550 µm and in one case about 500 µm. Thus, although dimensions can vary the cross sectional area can often range from about 1,000 to about 300,000 µm$^2$.

It is noted that, in some examples, it can be desirable to introduce the nucleic acid sample as a sample plug and pumped through the microfluidic pathway via plug flow. A motive fluid can be used to drive the plug in a desired direction at a desired rate. Where this is the case, the microfluidic device can optionally include a forward plug motive fluid inlet upstream of the first terminus. Alternatively, or additionally, the microfluidic device can optionally include a backward plug motive fluid inlet downstream of the second terminus. Thus, a motive fluid can be introduced on either side, or both sides, of the sample plug to facilitate movement of the sample through the microfluidic pathway. In some examples, a driving fluid source can be coupled to one, or both, plug motive fluid inlets.

Generally, the microfluidic pathway can be formed by cutting or etching a microchannel pattern in a suitable thin film, such as polyimide tape. Other thin films can also be used such as, but not limited to, silicones, glass, silicon and polymers that are thermally stable above at least 100° C. The thin film can then be coupled between two plates, such as glass or plastic plates, to form a microfluidic chip including the microfluidic pathway. The temperature regulator can be thermally associated with the microfluidic chip to prepare the microfluidic device.

A method of amplifying a nucleic acid is also described herein. The method can include introducing a nucleic acid sample into the bi-directional microfluidic serpentine pathway having a plurality of oscillation segments. Additionally, the method can include directing the nucleic acid sample along the bi-directional microfluidic serpentine pathway through a plurality of alternating high temperature zones and low temperature zones via the plurality of oscillation segments. The plurality of high temperature zones and low temperature zones can provide a temperature gradient suitable to amplify the nucleic acid. In some examples, the method is performed only after a steady state temperature is achieved.

In further detail, in some examples, the nucleic acid sample can be introduced into the bi-directional microfluidic serpentine pathway as a sample plug. Where this is the case, the sample plug can typically have a volume of from about 5 µl to about 100 µl. In some specific examples, the sample plug can have a volume of from about 10 µl to about 20 µl.

In some additional examples, a motive fluid can be injected or introduced into the microfluidic serpentine pathway before and/or after introducing the nucleic acid sample to form a motive fluid boundary on opposite sides of the nucleic acid sample within the pathway. A number of suitable motive fluids can be used including liquids or gases. Suitable motive fluids typically do not react with the plug and minimize or entirely avoid mixing with the plug fluid mass. Non-limiting examples of motive fluids can include air, nitrogen, argon, mineral oil, the like, or combinations thereof. In some specific examples, the microfluidic serpentine pathway can have a dead end terminus and the motive fluid can be a compressible gas introduced between the dead end terminus and the sample plug. Optionally, a motive fluid can be also be introduced between the sample plug and the inlet/outlet of the microfluidic serpentine pathway. In this example, when the microfluidic serpentine pathway is pressurized, the sample plug can move toward the dead end terminus and compress the gas between the sample plug and the dead end terminus. Driving force may need to be adjusted during the cycle in order to maintain desired residence times and flow rates. However, when the external pressure is relieved, the compressed gas can force the sample plug back toward the inlet/outlet. In yet other examples, the microfluidic serpentine pathway can include a fluid inlet/outlet at both termini. In this way, a motive fluid can be introduced at either terminus. In either scenario, it is possible to form a motive fluid boundary on opposite sides of the sample plug within the pathway.

The nucleic acid sample can generally include the nucleic acid (i.e. a target nucleic acid), a thermally stable polymerase, primers for amplification of the nucleic acid, and deoxynucleotide triphosphates (dNTPs). A "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU, dUTP, 7-deaza-dGTP), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA, or any combination thereof.

The polymerase of the nucleic acid sample can include any thermally stable polymerase. Non-limiting examples can include KlenTaq, Herculase, Kapa2G FAST, KOD Phusion, natural or cloned *Thermus aquaticus* polymerase, Platinum Taq, GoTaq, Fast Start, the like, or combinations thereof. The polymerase can generally be present at a concentration of from about 0.4 units (U)/µl to about 12 U/µl, where 1 unit is defined as 10 nmol of product synthesized in 30 minutes 72° C. The specific primers to extend the nucleic acid can be present in the nucleic acid sample in an amount from about 1.5 µM to about 20 µM. Each of the dNTPs (dATP, dCTP, dGTP, dTTP) can each be included in the nucleic acid sample in an amount from about 50 µM to about 500 µM.

In some examples, the nucleic acid sample can further include magnesium ions. Magnesium ions ($Mg^{++}$) can act as a cofactor in PCR. Thus, in some examples, the presence of magnesium ions can increase the productivity of the polymerase. Further, in some examples, magnesium ions can increase the annealing rate. Generally, the magnesium ion concentration in the nucleic acid sample can be from about 2 µM to about 7 µM.

In additional examples, the nucleic acid sample can include a fluorescent nucleic acid binding dye, a fluorescently labeled primer, a fluorescently labeled probe, or a combination thereof. Such fluorescent markers can be used to monitor various aspects of the PCR amplification process in real-time. In some specific examples, the nucleic acid can include a fluorescent nucleic acid binding dye. dsDNA binding dyes (i.e. dyes that fluoresce more strongly when bound to double-stranded DNA than when bound to single-stranded DNA or free in solution) may be used to detect dsDNA. Non-limiting examples of such dyes can include ethidium bromide, SYBR Green I, LCGreen, EvaGreen, YO-PRO-1, Hoechst 33258, SYBR Gold, SYTO9, the like, or combinations thereof. When excited by a particular wavelength of ultraviolet radiation, these dyes can emit fluorescent light, which can be detected via a fluorescence detector or other suitable detector in real-time to monitor the progress of the PCR amplification.

In some examples, the nucleic acid sample can include a fluorescently labeled probe or primer. By "probe" or "primer" is meant a single-stranded DNA or RNA molecule of defined sequence that can base-pair to a second DNA or RNA molecule that contains a complementary sequence (i.e. the target nucleic acid). The stability of the resulting hybrid depends upon the length, GC content, nearest neighbor stacking energy, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. As described above, probes and primers may be detectably-labeled, either radioactively, fluorescently, or non-radioactively, by methods well known to those skilled in the art. It is understood that a "primer" is specifically configured to be extended by a polymerase, whereas a "probe" may or may not be so configured.

The nucleic acid sample can generally include components and associated concentrations suitable for extreme PCR. Such components, concentrations, conditions, etc. are described in greater detail in U.S. Patent Publication 2015/0118715 and U.S. Patent Publication 2016/0289736, each of which is incorporated herein by reference.

In some examples, the nucleic acid sample can be pumped through the microfluidic serpentine pathway in bi-directional flow. However, in some examples, unidirectional flow may be adequate depending on the number of oscillation segments present along the microfluidic serpentine pathway. Generally, each of the oscillation segments provides a PCR amplification cycle. However, as described above, this can depend on whether the oscillation segment intersects the temperature gradient formed between high temperature zones or regions and low temperature zones or regions. It is noted that, in some cases, individual or a plurality of high temperature zones intersected by the pathway can be formed from a common high temperature region. Similarly, individual or a plurality of low temperature zones intersected by the pathway can be formed from a common low temperature region. In some other examples, each high temperature zone or low temperature zone can be generated from distinct temperature regulators positioned at that zone, each of which can be individually controlled. In some examples, one or more temperature regulators can be turned off such that a portion of the oscillation segments does not provide a PCR amplification cycle due to an inadequate temperature gradient across the oscillation segment. As such, in some examples, a portion of the oscillation segments may not intersect with the temperature gradient and fail to provide a PCR amplification cycle. Although target temperatures can vary depending on the polymerase, primers, etc. typical high temperature region temperatures can range from about 60 to 120° C. Similarly, the low temperature region can be maintained within about 35 to about 75° C.

Thus, the number of oscillation cycles, or active oscillation cycles, present along the microfluidic serpentine pathway can also determine the number of times the sample is passed or cycled through the microfluidic serpentine pathway. For example, in some cases, a single unidirectional pass through the microfluidic pathway can be adequate to achieve suitable levels of nucleic acid amplification. In other examples, a single device cycle (i.e. once forward and back) through the microfluidic pathway can be adequate to achieve suitable levels of nucleic acid amplification. However, in some examples, multiple device cycles may be needed or desirable. For example, in some cases, the nucleic acid sample can be cycled through the microfluidic serpentine pathway for a plurality of device cycles. Again, the number of device cycles is dependent on the number of active oscillation segments present along the microfluidic serpentine pathway. In some examples, the plurality of device cycles can include from 1 device cycle to 5 device cycles or 10 device cycles. In yet other examples, the plurality of device cycles can include from 2 device cycles to 50 device cycles, from 3 device cycles to 20 device cycles, or from 4 device cycles to 8 device cycles.

In some examples, the average time per PCR amplification cycle can also depend on the number of active oscillation segments (i.e. the number of oscillation segments intersecting the temperature gradient) are present along the microfluidic serpentine pathway. For example, where a given microfluidic serpentine pathway includes 10 oscillation segments and the nucleic acid sample is passed through the entire length of the pathway in one direction in a period of time of 20 seconds, an average of one PCR cycle every two seconds is possible. However, where half of the oscillation segments are inactive because one or more temperature regulators have been turned off, the number of PCR amplification cycles can drop by half and decrease the average number of PCR amplification cycles to one cycle every four seconds. Generally, the present method can achieve an average rate of from about 1 PCR amplification cycle every 0.25 seconds to about 1 PCR amplification cycle every 8 seconds. In specific examples, the present method can achieve an average rate of from about 1 PCR amplification cycle every 0.5 seconds to about 1 PCR amplification cycle every 4 seconds, or from about 1 PCR amplification cycle every 1 second to about 1 PCR amplification cycle every 2 seconds. In some examples, the present method can achieve from about 1 PCR amplification cycle every 4 seconds or less, every 2 seconds or less, or every 1 second or less.

In some examples, the method can further include monitoring amplification of the nucleic acid to generate an amplification feedback report. In such examples, the microfluidic device can be operatively associated with a fluorescence detector or other suitable detector that can monitor the overall progress of PCR amplification. For example, as discussed above, dsDNA binding dyes fluoresce more strongly when bound to double-stranded DNA than when bound to single-stranded DNA or free in solution. Thus, these dyes, or fluorescently labeled primers or probes, can be used to monitor the progress of nucleic acid amplification, such as rate of amplification and amount of amplification. Specifically, the rate at which the fluorescence signal from the nucleic acid sample intensifies can correspond to the rate at which nucleic acid amplification is occurring. Similarly, the intensity of the fluorescence signal can correspond to the amount of nucleic acid present.

As such, the rate of amplification and the amount of amplification can be monitored in real-time and can be used in a system with closed loop feedback. Specifically, an amplification feedback report can be generated based on the progress of the nucleic acid amplification. In some examples, the amplification feedback report may indicate that the rate at which amplification is occurring is less than optimal. In such cases, the amplification feedback report can generate a feedback communication within the system to adjust the temperature gradient to change a rate of nucleic acid amplification. Similarly, the system can be programmed to achieve a particular amount of nucleic acid amplification, which can be correlated to the intensity of the fluorescence signal from the nucleic acid sample. Accordingly, the amplification feedback report can generate a feedback communication within the system to adjust the number of times the nucleic acid sample passes or cycles through the microfluidic serpentine pathway to achieve a target number of amplicons or a minimum concentration of nucleic acid within the nucleic acid sample. Additionally, where appropriate, the amplification feedback report can generate a feedback communication with the system to turn specific temperature regulators on or off to achieve a target number of PCR amplification cycles, rate of amplification, etc.

EXAMPLE

A microfluidic chip was made by cutting the microchannel in polyimide tape (double-side adhesive) by a knife plotter and then bonded between two microscope glass slides. The lower glass slide is spray painted dull black so that the plug of PCR mix was easily visible to the naked eye. In addition, the 20-cycle chip (i.e. 20 oscillation segments) was simulated in COMSOL Multiphysics in 3D domain at steady state to provide an approximation for attainment of reaction temperatures important for a successful PCR reaction. This COMSOL model was based on a heat transfer model recently published to study the effects of key variables affecting the functionality of thermal gradient continuous flow PCR systems. Based on the simulation, the desired thermal gradient was determined and a heating instrumentation was used to produce that thermal gradient across the chip in order to amplify a specific product. The PCR reaction mix was only run through the chip (in a back and forth fashion) when the steady state gradient was established.

A 102 bp NQ01 gene of the human genome was used to test the system for extreme PCR. The starting template concentration was 2500 copies/ul in a reaction volume of ~15 ul. The sample was cycled once back and forth to complete 40 PCR amplification cycles. Total time to complete was between 40 and 80 seconds. Once all cycles were completed the product was melted in a commercial high resolution melting analysis system for product identification.

Figure 3A:
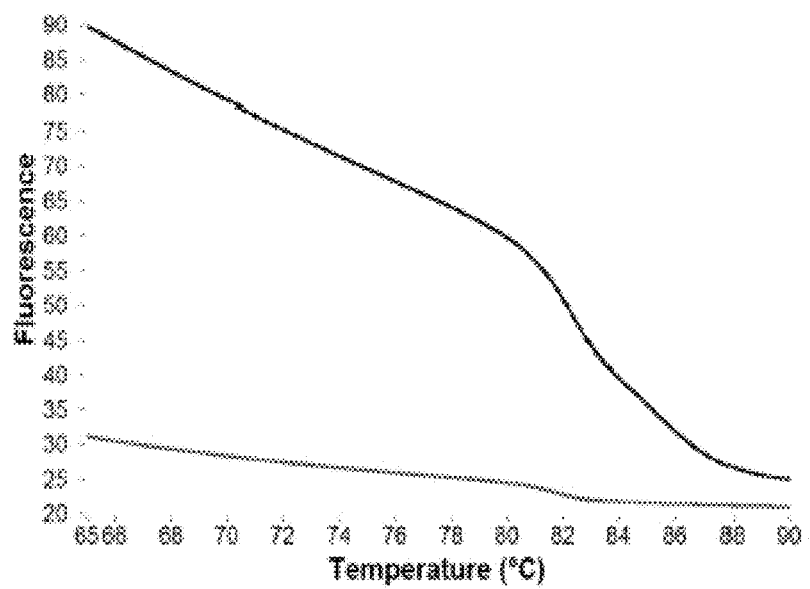
FIG. 3A is a graph of a melt curve for a PCR product obtained via an example microfluidic device.
Figure 3B:
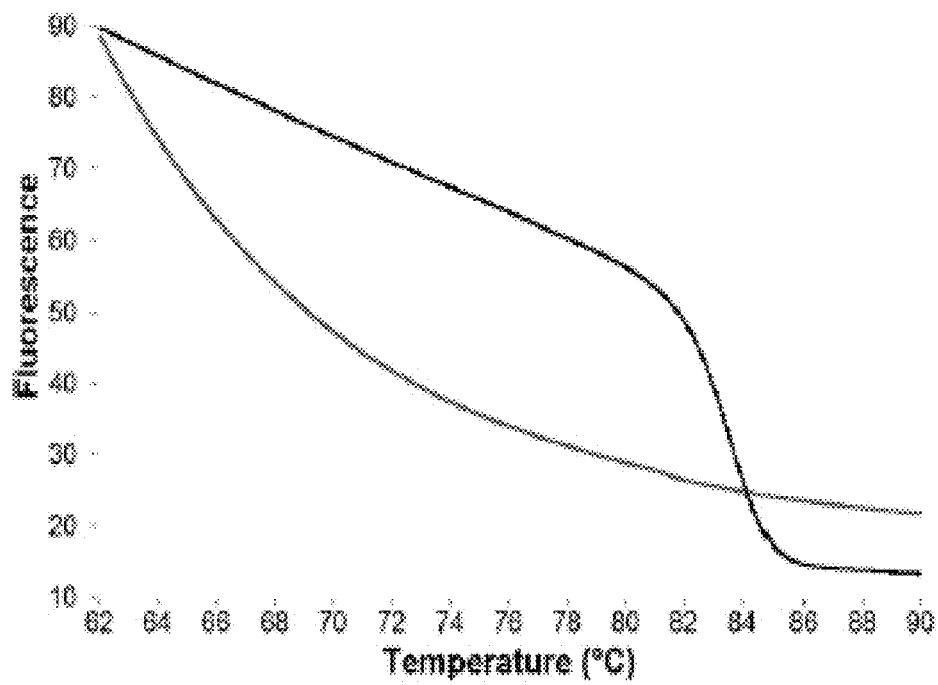
FIG. 3B is a graph of a melt curve for a PCR product not obtained via a microfluidic device.
Figure 3C:
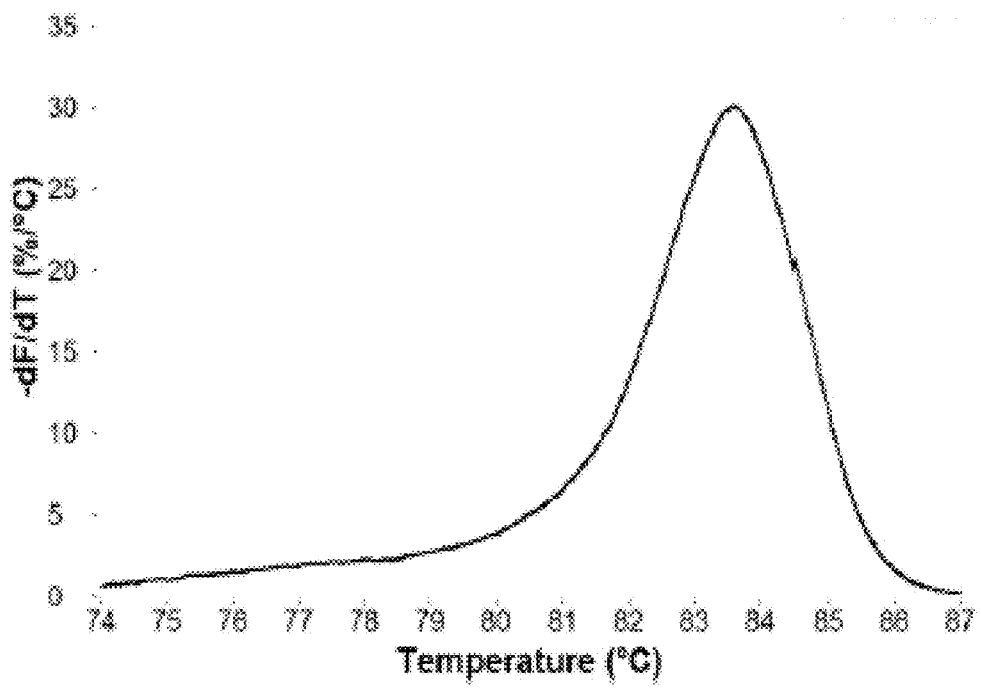
FIG. 3C is a graph of a melt curve for a PCR product obtained via an example microfluidic device.

FIG. 3A shows the PCR product+probe (upper curve) and negative control+probe (lower curve) that were run through the chip. The probe was used to further confirm the identification of the PCR product. FIG. 3B shows the PCR product (upper curve) and negative control (lower curve) that were not run through the chip. FIG. 3C shows the PCR product with a distinct peak based on the derivative of fluorescence intensity with respect temperature against temperature.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A microfluidic device, comprising:
a temperature regulator positioned to generate a temperature gradient across a thermally controlled portion of the microfluidic device from a high temperature region to a low temperature region; and
a bi-directional microfluidic serpentine pathway having a first terminus and a second terminus oriented along a longitudinal direction transverse to the temperature gradient, said microfluidic pathway including a plurality of oscillation segments fluidly coupling the first terminus to the second terminus and forming a flow path adapted to oscillate a fluid between the high temperature region and the low temperature region, wherein the microfluidic pathway has a uniform cross-section to facilitate bi-directional fluid flow.

2. The microfluidic device of claim 1, wherein the temperature regulator is selected from the group consisting of an electrical resistor, a Peltier heat pump, a heat transfer fluid, and combinations thereof.

3. The microfluidic device of claim 1, further comprising a metal plate adjacent a common plane of the device to form an offset heat transfer path.

4. The microfluidic device of claim 1, wherein the temperature regulator comprises a plurality of individually controllable temperature regulators.

5. The microfluidic device of claim 1, further comprising a temperature sensor thermally positioned to monitor a temperature of the microfluidic device.

6. The microfluidic device of claim 1, wherein the bi-directional microfluidic serpentine pathway is longitudinally symmetrical.

7. The microfluidic device of claim 1, wherein the bi-directional microfluidic serpentine pathway is positioned within a common plane.

8. The microfluidic device of claim 1, wherein the bi-directional microfluidic serpentine pathway comprises a right-angle bend having a squared corner within each of the plurality of oscillation segments.

9. The microfluidic device of claim 1, wherein one of the first terminus and the second terminus is not an inlet/outlet.

10. The microfluidic device of claim 1, wherein the plurality of oscillation segments forms peaks and troughs along the serpentine pathway within a common plane.

11. The microfluidic device of claim 1, wherein each of the plurality of oscillation segments includes a first lateral segment directing fluid to the high temperature region, a second lateral segment directing fluid to the low temperature region, and a first longitudinal segment fluidly interconnecting the first lateral segment and the second lateral segment within the high temperature region.

12. The microfluidic device of claim 1, wherein each of the plurality of oscillation segments is positioned within the thermally controlled portion of the device.

13. The microfluidic device of claim 1, comprising from 5 oscillation segments to 20 oscillation segments.

14. The microfluidic device of claim 1, wherein the uniform cross-section is from about 1000 $\mu m^2$ to about 300,000 $\mu m^2$.

15. The microfluidic device of claim 1, further comprising a forward plug motive fluid inlet upstream of the first terminus and a backward plug motive fluid inlet downstream of the second terminus.

16. A method of amplifying a nucleic acid, comprising:
introducing a nucleic acid sample into a microfluidic serpentine pathway having a plurality of oscillation segments and a uniform cross-section to facilitate bi-directional fluid flow, said nucleic acid sample comprising the nucleic acid; and
directing the nucleic acid sample along the microfluidic serpentine pathway through a plurality of alternating high temperature zones and low temperature zones via the plurality of oscillation segments, said plurality of alternating high temperature zones and low temperature zones providing a temperature gradient suitable to amplify the nucleic acid.

17. The method of claim 16, wherein the nucleic acid sample is introduced as a sample plug.

18. The method of claim 17, further comprising injecting a motive fluid into the microfluidic serpentine pathway before and after introducing the nucleic acid sample to form a motive fluid boundary on opposite sides of the nucleic acid sample within the pathway.

19. The method of claim 18, wherein the motive fluid is a member selected from the group consisting of air, mineral oil, nitrogen, and combinations thereof.

20. The method of claim 16, wherein each of the oscillation segments that intersects the temperature gradient provides one polymerase chain reaction (PCR) amplification cycle.

21. The method of claim 20, wherein a portion of the oscillation segments does not intersect with the temperature gradient and does not provide a PCR amplification cycle.

22. The method of claim 20, wherein each of the plurality of oscillation segments provides a PCR amplification cycle.

23. The method of claim 20, each PCR amplification cycle is performed at an average rate of from 1 amplification cycle/0.25 seconds to 1 amplification cycle/8 seconds.

24. The method of claim 16, wherein each of the high temperature zones is formed from a common high temperature region and each of the low temperature zones is formed from a common low temperature region.

25. The method of claim 16, wherein the nucleic acid sample further comprises a thermally stable polymerase, primers for amplification of the nucleic acid, and deoxynucleotide triphosphates (dNTPs).

26. The method of claim 16, wherein the nucleic acid sample further comprises magnesium ions.

27. The method of claim 16, wherein the nucleic acid sample further comprises a fluorescent nucleic acid binding dye, a fluorescently labeled primer, a fluorescently labeled probe, or a combination thereof.

28. The method of claim 16, wherein directing comprises bi-directional fluid flow.

29. The method of claim 16, wherein directing comprises cycling the nucleic acid through the microfluidic serpentine pathway for a plurality of device cycles.

30. The method of claim 29, wherein the plurality of cycles is from 2 device cycles to 50 device cycles.

31. The method of claim 16, further comprising monitoring amplification of the nucleic acid to generate an amplification feedback report.

32. The method of claim 31, wherein the amplification feedback report is adapted to adjust the temperature gradient to change a rate of nucleic acid amplification.

33. The method of claim 31, wherein the amplification feedback report is adapted to adjust a number of passes through the microfluidic serpentine pathway to achieve a minimum concentration of nucleic acid within the nucleic acid sample.

* * * * *